(12) United States Patent
Geitz

(10) Patent No.: US 7,918,866 B2
(45) Date of Patent: Apr. 5, 2011

(54) DEVICES AND RELATED METHODS FOR SECURING A TISSUE FOLD

(75) Inventor: Kurt E. Geitz, Sudbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1061 days.

(21) Appl. No.: 11/715,966

(22) Filed: Mar. 9, 2007

(65) Prior Publication Data

US 2007/0162073 A1   Jul. 12, 2007

Related U.S. Application Data

(63) Continuation of application No. 10/419,105, filed on Apr. 21, 2003, now Pat. No. 7,204,842, which is a continuation of application No. 09/568,012, filed on May 10, 2000, now Pat. No. 6,592,596.

(51) Int. Cl.
*A61B 17/10* (2006.01)
*A61B 17/08* (2006.01)

(52) U.S. Cl. .......................................... 606/142; 606/153

(58) Field of Classification Search ................... 606/139, 606/142, 153, 219; 227/175.1, 178.1, 180.1, 227/181.1
See application file for complete search history.

(56) References Cited

U.S. PATENT DOCUMENTS

| | | | |
|---|---|---|---|
| 3,571,861 A | 3/1971 | Olson | |
| 4,402,445 A | 9/1983 | Green | |
| 4,512,345 A | 4/1985 | Green | |
| 4,573,622 A | 3/1986 | Green et al. | |
| 4,606,345 A | 8/1986 | Dorband et al. | |
| 4,612,933 A | 9/1986 | Brinkerhoff et al. | |
| 4,635,634 A | 1/1987 | Santos | |
| 4,741,336 A | 5/1988 | Failla | |
| 4,932,960 A | 6/1990 | Green et al. | |
| 5,027,834 A | 7/1991 | Pruitt | |
| 5,040,715 A | 8/1991 | Green et al. | |

(Continued)

FOREIGN PATENT DOCUMENTS

EP    0 442 588 A2    8/1991

OTHER PUBLICATIONS

J. Barry McKernan M.D., Ph.D., J. Kenneth Champion, M.D., "Laparosocpic Antireflux Surgery," *The American Surgeon*, vol. 61, pp. 530-536, Jun. 1995.

*Primary Examiner* — Julian W Woo
(74) *Attorney, Agent, or Firm* — Finnegan Henderson Farabow Garrett & Dunner, L.L.P.

(57) ABSTRACT

The present invention relates to devices and methods for creating and securing a tissue fold during an endoluminal medical procedure. The devices and methods may be used for folding and securing, for example, a fundus wall onto an esophagus wall. An aspect of the invention includes a two-piece tissue clip configured to be installed through an endoluminal device to secure a tissue fold. The clip includes a female member and a male member configured to engage one another to secure the tissue fold. Another aspect of the invention includes a clipping device comprising a tissue clip magazine. The magazine is configured to hold a plurality of tissue clips and install the plurality of tissue clips in a single actuation of the magazine. A method for using the clipping device together with the tissue clips of the present invention to create and secure a fold of tissue during an endoluminal procedure also is disclosed.

20 Claims, 5 Drawing Sheets

U.S. PATENT DOCUMENTS

| | | |
|---|---|---|
| 5,100,420 A | 3/1992 | Green et al. |
| 5,114,065 A | 5/1992 | Storace |
| 5,250,058 A | 10/1993 | Miller et al. |
| 5,258,012 A | 11/1993 | Luscombe et al. |
| 5,292,053 A | 3/1994 | Bilotti et al. |
| 5,336,233 A | 8/1994 | Chen |
| 5,344,060 A | 9/1994 | Gravener et al. |
| 5,350,104 A | 9/1994 | Main et al. |
| 5,355,897 A | 10/1994 | Pietrafitta et al. |
| 5,358,496 A | 10/1994 | Ortiz et al. |
| 5,403,326 A | 4/1995 | Harrison et al. |
| 5,423,858 A | 6/1995 | Bolanos et al. |
| 5,465,894 A | 11/1995 | Clark et al. |
| 5,478,354 A | 12/1995 | Tovey |
| 5,484,095 A | 1/1996 | Green et al. |
| 5,571,116 A | 11/1996 | Bolanos et al. |
| 5,676,674 A | 10/1997 | Bolanos et al. |
| 5,833,696 A | 11/1998 | Whitfield et al. |
| 5,855,565 A | 1/1999 | Bar-Cohen et al. |
| 5,957,363 A | 9/1999 | Heck |
| 6,050,472 A | 4/2000 | Shibata |
| 6,086,600 A | 7/2000 | Kortenbach |
| 6,117,148 A | 9/2000 | Ravo et al. |
| 6,119,913 A | 9/2000 | Adams et al. |
| 6,176,413 B1 | 1/2001 | Heck et al. |
| 6,253,984 B1 | 7/2001 | Heck et al. |
| 6,264,086 B1 | 7/2001 | McGuckin, Jr. |
| 6,280,415 B1 | 8/2001 | Johnson |
| 6,478,210 B2 | 11/2002 | Adams et al. |
| 6,663,639 B1 | 12/2003 | Laufer et al. |
| 2002/0016603 A1 | 2/2002 | Wells |
| 2002/0055752 A1 | 5/2002 | Schraft et al. |
| 2002/0082621 A1 | 6/2002 | Schurr et al. |
| 2002/0082625 A1 | 6/2002 | Huxel et al. |
| 2002/0156344 A1 | 10/2002 | Pasricha et al. |
| 2002/0177859 A1 | 11/2002 | Monassevitch et al. |
| 2003/0040764 A1 | 2/2003 | Adams |
| 2003/0220657 A1 | 11/2003 | Adams |
| 2004/0059358 A1 | 3/2004 | Kortenbach et al. |

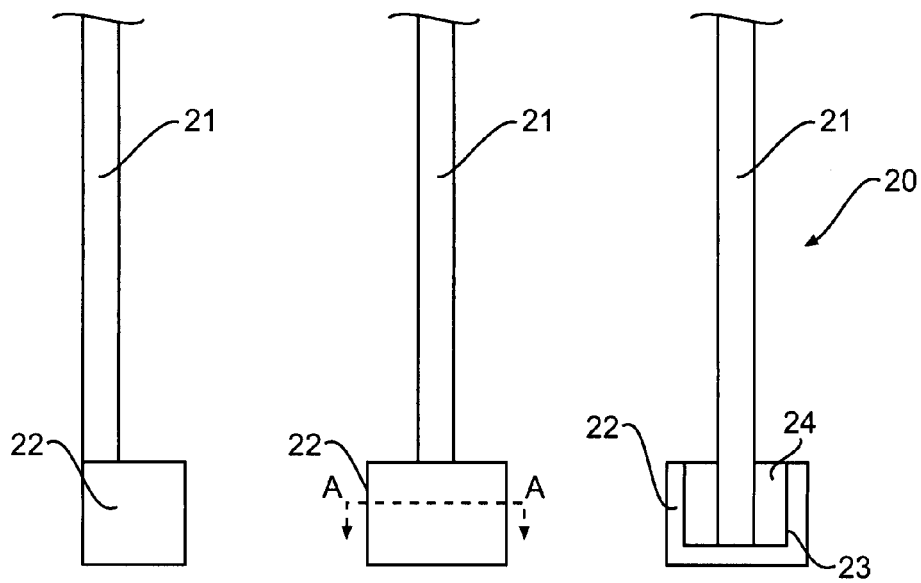
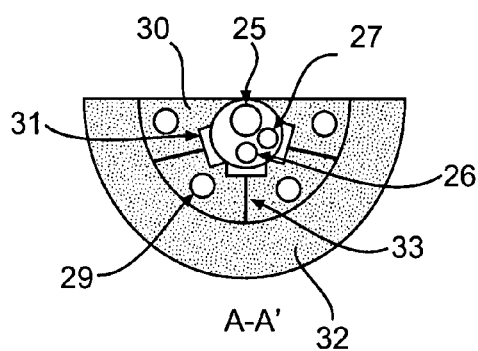
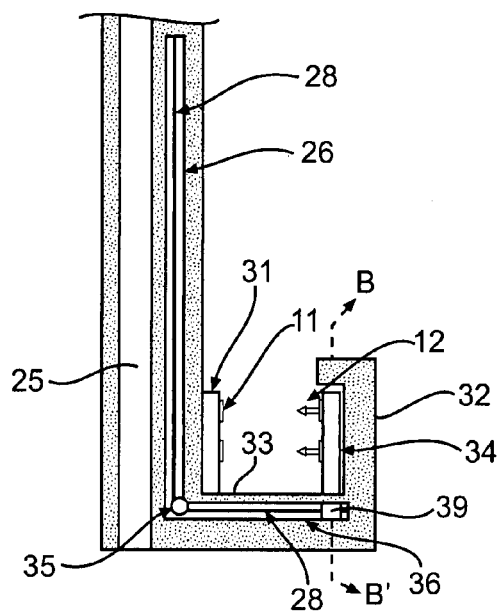
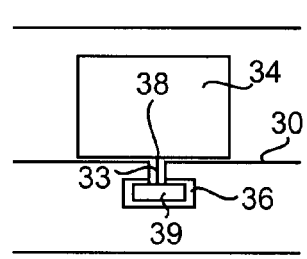
FIG. 3A   FIG. 3B   FIG. 3C
FIG. 4
FIG. 5B
FIG. 5A

DEVICES AND RELATED METHODS FOR SECURING A TISSUE FOLD

This is a continuation of application Ser. No. 10/419,105, filed Apr. 21, 2003, now U.S. Pat. No. 7,204,842 which is a continuation of application Ser. No. 09/568,012, filed May 10, 2000, now U.S. Pat. No. 6,592,596, all of which are incorporated herein by reference.

FIELD OF THE INVENTION

The present invention pertains to devices, and a method for using the devices, for creating and securing a tissue fold during an endoluminal procedure. More specifically, the invention relates to devices and methods for folding, for example, a region of the stomach circumferential to the opening of the esophagus back onto the esophagus.

BACKGROUND OF THE INVENTION

Gastroesophageal reflux occurs when stomach acid enters the esophagus. This reflux of acid into the esophagus occurs naturally in healthy individuals, but also may become a pathological condition in others. Effects from gastroesophageal reflux range from mild to severe. Mild effects include heartburn, a burning sensation experienced behind the breastbone. More severe effects include a variety of complications, such as esophageal erosion, esophageal ulcers, esophageal stricture, abnormal epithelium (e.g., Barrett's esophagus), esophageal cancer, and/or pulmonary aspiration. These various clinical conditions and changes in tissue structure that result from reflux of stomach acid into the esophagus are referred to generally as Gastroesophageal Reflux Disease (GERD).

Many mechanisms contribute to prevent gastroesophageal reflux in healthy individuals. One such mechanism is the functioning of the lower esophageal sphincter (LES). With reference to FIG. 1, the LES is a region of smooth muscle and increased annular thickness existing in the last four centimeters of the esophagus. In its resting state, the LES creates a region of high pressure (approximately 15-30 mm Hg above intragastric pressure) at the opening of the esophagus into the stomach. This pressure essentially closes the esophagus so that contents of the stomach cannot pass back into the esophagus. The LES opens in response to swallowing and peristaltic motion in the esophagus, allowing food to pass into the stomach. After opening, however, a properly functioning LES should return to the resting, or closed state. Transient relaxations of the LES do occur in healthy individuals, however, typically resulting in normal physiological functions such as belching and vomiting.

The physical interaction occurring between the gastric fundus and the esophagus also prevents gastroesophageal reflux. The gastric fundus is a lobe of the stomach situated at the top of the stomach proximal to the esophagus. In healthy individuals, the fundus presses against the opening of the esophagus when the stomach is full of food and/or gas. This effectively closes off the esophageal opening to the stomach and helps to prevent acid reflux back into the esophagus.

In individuals with GERD, the LES functions abnormally, either due to an increase in transient LES relaxations, decreased muscle tone of the LES during resting, or an inability of the esophageal tissue to resist injury or repair itself after injury. More generally, GERD results from a change in the geometrical relationship between the esophagus and the fundus of the stomach. Normally, the fundus extends above the exit of the esophagus into the stomach. Thus, as intra-abdominal pressure increases, the fundus pushes against the LES to assist in closing the LES. In people with GERD, the fundus flattens out so that it no longer assists in closing the fundus. Moreover, the LES tends to shorten from about 4 cm to about 2 cm in length. GERD can also be caused by hiatel hernia, which also may potentially lead to a change in the geometric relationship as described above. These conditions often are exacerbated by overeating, intake of caffeine, chocolate or fatty foods, and/or smoking. Avoiding these exacerbating mechanisms helps reduce the negative side effects associated with GERD, but does not cure the disease completely.

A surgical procedure, known generally as fundoplication, has been developed to prevent acid reflux in patients whose normal LES functioning has been impaired. Fundoplication involves bringing the fundus into closer proximity to the esophagus to help close off the esophageal opening into the stomach. In Nissen Fundoplication, a particular type of the fundoplication procedure, the fundus is pulled up and around the esophagus and sutured both to itself and to the esophagus such that it completely encircles the esophagus. Traditionally, this procedure has been performed as an open surgery, but has recently enjoyed success as a laparoscopic procedure, as discussed in McKernan, J. B., Champion, J. K., "Laparoscopic antireflex surgery," *American Surgeon*, Vol. 61, pp. 530-536, (1995).

As with any open surgery, the risks attendant in such a procedure are great. Due to relatively large incisions necessary in the performance of open surgery, relatively large amounts of blood are lost and risk of infection increases. Though laparoscopic surgical procedures reduce these negative effects by using relatively small devices at a relatively small incision site in the abdominal wall, there still exists an increased risk of infection due to the incision. The location of the incision in the abdominal wall presents a risk of other negative effects, such as sepsis, which can be caused by leakage of septic fluid contained in the stomach. Furthermore, as with any surgery, there exists a small risk of morbidity and mortality associated with the use of general anasthesia.

SUMMARY OF THE INVENTION

The advantages and purpose of the present invention will be set forth in part in the description which follows, and in part will be obvious from the description, or may be learned by practice of the invention. The advantages and purpose of the invention will be realized and attained by means of the elements and combinations particularly pointed out in the appended claims.

The present invention includes devices, and related methods for using the devices, to fold and secure tissue during an endoluminal medical procedure. In particular, the inventive devices, and the methods for using the devices, may be employed in Nipple Fundoplication procedures, a specific type of fundoplication procedure which will be described shortly, for the treatment of GERD. When used to perform, for example, Nipple Fundoplication, the inventive devices allow the procedure to be completed rapidly, repeatedly, and consistently without compromising safety or increasing invasiveness.

To attain the advantages and in accordance with the purpose of the invention, as embodied and broadly described herein, the invention includes a device for securing a fold of tissue comprising a female member and a male member. The female member defines an aperture and the male member has an. engaging member configured to pierce and extend through a fold of tissue. The aperture and engaging member are configured so as to allow the engaging member to pass through the aperture in a first direction when the female and male members are in a disengaged relationship and to restrict the engaging member from passing through the aperture in a second direction opposite to the first direction when the female and male members are in an engaged relationship.

Another aspect of the invention includes a clipping device for creating and securing a tissue fold. The clipping device includes a tube having a magazine disposed on its distal end. The magazine is configured to hold a plurality of tissue clips for installation to secure the tissue fold. An actuator, disposed at a proximal end of the shaft, actuates the magazine to simultaneously install the plurality of tissue clips.

Yet another aspect of the invention includes a method for securing a tissue fold during an endoluminal medical procedure. The method includes providing a plurality of tissue clips configured to engage and secure a tissue fold, and providing a tissue clip magazine configured to hold the plurality of tissue clips. The method further includes inserting the tissue clip magazine using an endoluminal procedure into an area of the body where a tissue field is to be secured. The magazine is then positioned proximal to the tissue fold and actuated such that the plurality of tissue clips are simultaneously installed with respect to the tissue fold.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate the preferred embodiments of the invention and, together with the description, serve to explain the principles of the invention. In the drawings.

FIGS. 3a-3c are respective side, front, and rear views of an embodiment of a clipping device according to the present invention;

FIG. 4 is a cross-sectional view taken through plane A-A' in FIG. 3b showing details of the internal structure of the embodiment of the clipping device according to the present invention;

FIG. 5a is cross-sectional side view of an embodiment of the clipping device with tissue clips inserted according to the present invention;

FIG. 5b is a cross-section view of FIG. 5a taken through line B-B';

DESCRIPTION OF THE PREFERRED EMBODIMENTS

A newly developed form of fundoplication, referred to as Nipple Fundoplication, is an endoluminal procedure in which the fundus is folded back onto the esophagus. The tissue fold formed between the esophagus and fundus is then secured. Nipple Fundoplication is intended to be performed as an endoluminal procedure, with insertion of required medical instruments occurring through the esophagus. Such a procedure has the benefits of being less invasive, quicker, and less expensive as compared to previous techniques.

As with most endoluminal procedures, preferably, completion of Nipple Fundoplication occurs as rapidly as possible without compromising the safety or non-invasiveness of the procedure. To maintain the procedure as relatively non-invasive, it is preferable to provide a device, and method for using the device, that is small in size, yet has the capability to secure the fundus to the esophagus in a plurality of locations during a single insertion and with consistent results.

The various aspects of this invention pertain generally to a tissue clip and a clipping device for installing the tissue clip to create and secure a tissue fold during an endoluminal procedure. The devices, and methods for their use, are particularly suited for performing the Nipple Fundoplication procedure described previously. Using the inventive devices to secure the fundus to the esophagus in Nipple Fundoplication allows the procedure to be performed rapidly and relatively non-invasively, and results in a substantially uniform tissue fold.

To accomplish these objectives, the present invention includes a tissue clip and a clipping device adapted to position the tissue clip to secure the fold of tissue created during the endoluminal procedures Additionally, the present invention includes a method for using the tissue clip and the clipping device. Although, the inventive devices will be discussed mainly with reference to their use in securing a fundus wall to an esophagus wall in a Nipple Fundoplication procedure, the devices can be used in conjunction with other medical procedures that require creating and securing tissue folds. Moreover, the devices may be used in other settings, including industrial settings, that require the securing of two surfaces together in an environment having limited access to the two surfaces.

Figure 1:
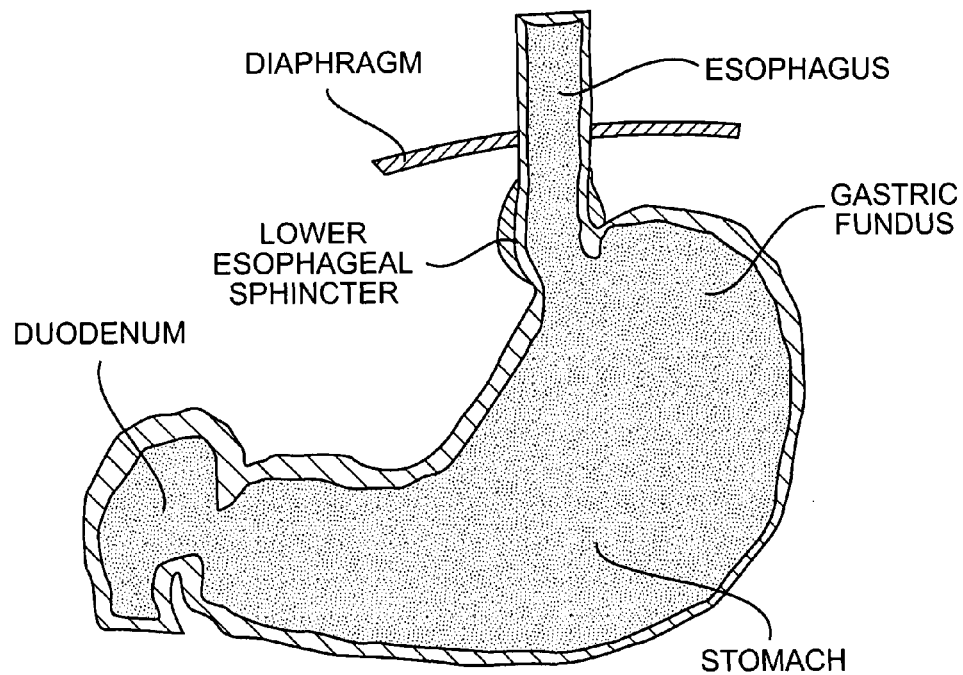
FIG. 1 is a cross-sectional view of the gastrointestinal tract from a mid-point of the esophagus to a point near the beginning of the duodenum.
Figure 2:
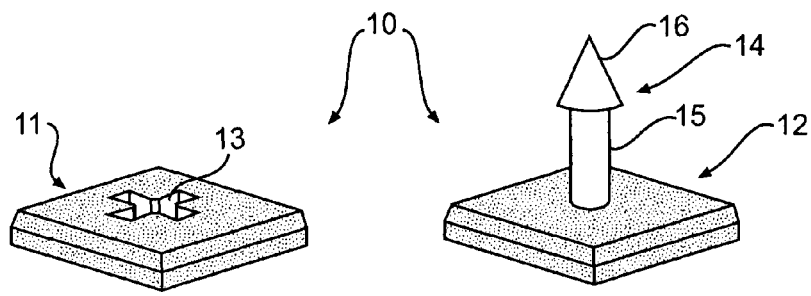
FIG. 2 is a perspective view of a respective female member and male member that form a tissue clip according to an embodiment of the present invention.
Figure 6:
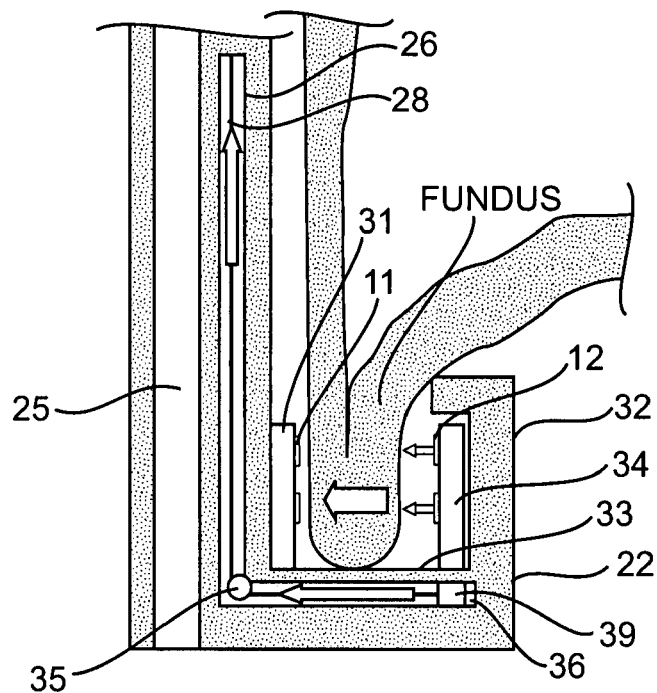
FIG. 6 is a cross-sectional side view of the clipping device of FIG. 5a, with an upward force exerted on the cable to move a sliding clip holder toward a stationary clip holder.
Figure 7:
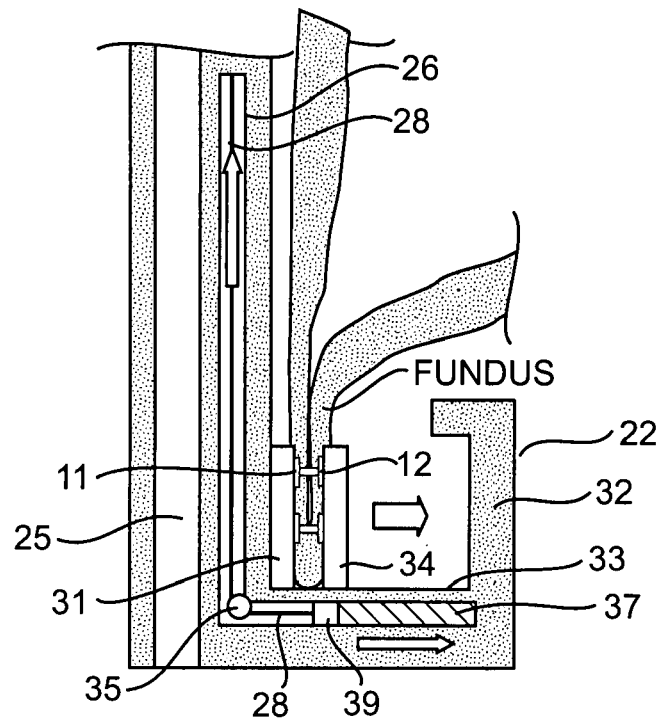
FIG. 7 is a cross-sectional side view of the clipping device of FIG. 5a after the female and male members of the tissue clip have been engaged to secure the tissue fold and the upward force has been released to cause the sliding clip holder to spring back into its original position.

A preferred embodiment of a tissue clip 10 according to the present invention is shown in FIG. 2. Tissue clip 10 includes two members, a female member 11 and a male member 12. Members 11 and 12 essentially have plate-shaped configurations, shown as square plates in the Figure. Female member 11 includes an X-shaped aperture 13 disposed substantially in the center of the member and extending through its thickness. Male member 12 includes an engaging member 14 disposed substantially in the center of male member 12 and extending perpendicularly from its surface. Engaging member 14 includes a stem portion 15 and a head portion 16 extending from stem portion 15. Head portion 16 has a tapered shape, with the widest part of the taper closest to the stem. Aperture 13 and engaging member 14 are sized and shaped to allow engaging member 14 to pass through aperture 13 when female member 11 and male member 12 start from a disengaged relationship. Once engaging member 14 has passed through aperture 13 such that female member 11 and male member 12 are in an engaged relationship, head portion 15, at the widest part of the taper, abuts the surface of member 11 surrounding aperture 13. Thus engaging member 14 cannot pass back through aperture 13 in a direction opposite to the direction it passed through initially.

Tissue clip 10 can be made of any suitable material that is biocompatible, such as polyethylene, teflon, or titanium. However, due to the high mobility of the LES and the concomitant incidence of implant migration, it is more preferable to use materials that are bioabsorbable, such as, polydioxanone, poly e-caprolactone, polylactic acid, polyglycolic acid or poly(DL-lactide-coglycolide), or combinations or mixtures thereof. When a bioabsorbable material is used to make tissue clip 10, it is contemplated that eventually adhesions will form between the tissue on the esophagus wall and the fundus wall such that external securing means, such as the clip, are unnecessary. Thus, the bioabsorbable material should be selected such that disintegration of the clip occurs after the tissue has had an opportunity to fully adhere.

In general, tissue clip 10 has dimensions that allow it to be used with endoluminal devices and for the purposes of securing the fold created during a fundoplication procedure. A preferred form of tissue clip 10 has dimensions that prevent ischemia of the tissue between the clip plates while still enabling it to be inserted and installed using a clipping device 20 according to the present invention, which will be discussed shortly. The plates forming tissue clip 10 each have a length of approximately 1 cm and a width of approximately 5 mm. Additionally, engaging member 14 must have a length that enables it to extend through the entire thickness of the tissue fold to be secured.

As mentioned previously, tissue clip 10, shown in the embodiment of FIG. 2, has an essentially square shape. However, the clip can have other shapes and the male and female members need not have the same shape. In fact, to avoid piercing of the tissue and subsequent migration, it is preferred to use a clip with rounded corners. Also, the embodiment shown has only a single aperture and a single engaging member that engage with one another. The scope of the invention includes any number of engaging members and apertures to secure the male and female members together. The number may be chosen based on factors such as, for example, the shape of the members, the size of the members, the thickness of the tissue to be folded, the area of the folded tissue to be secured, and other similar factors, and it has been found that two engaging members and two apertures are preferred to fix the position of the clip and to better resist migration.

An embodiment of a clipping device according to the present invention and adapted for use with the inventive tissue clip described above is shown in FIGS. 3-7. External side, front, and rear views of a clipping device 20 are shown in FIGS. 3a-3c, respectively. The embodiment of clipping device 20 generally includes a tube 21 and a tissue clip magazine 22 on a distal end of tube 21. Tissue clip magazine 22 is configured to hold tissue clips 10 during insertion and installation of the clips to secure the tissue fold. Tissue clip magazine 22 preferably has a substantially hollow semi-circular shape to facilitate insertion into the cylindrical shape of the esophagus. As shown in FIG. 3c, a back portion 23 of tissue clip magazine 22 is open so that tissue clips may easily be inserted into the magazine. Tissue clip magazine 22 also includes an opening 24 in the top of the magazine so that the fold of tissue can be seated within the magazine during installation of the tissue clip. Tissue clip magazine 22 engages tube 21 such that tube 21 lies substantially flush with back portion 23.

FIG. 4 illustrates details of the structure of clipping device 20, as seen from a cross-sectional perspective taken through plane A-A' in FIG. 3b, looking down toward a base of tissue clip magazine 22. As shown, tube 21 includes three lumens that extend longitudinally through tube 21. Specifically, tube 21 includes an endoscope lumen 25 for receiving an endoscope to provide vision into the body during use of clipping device 20. A cable lumen 26 also is provided in tube 21 for feeding a cable 28 (see FIG. 5) from an actuating mechanism (not shown), such as a spool with a knob to take up the cable, at a proximal end of tube 21 to a pulley-slider track system at the distal end. The third lumen in tube 21 is a vacuum supply lumen 27 which is in fluid communication with a vacuum source (not shown) at a proximal end of clipping device 20 and with suction ports 29 disposed on base 30 of tissue clip magazine 22. Sealed ducts (not shown), disposed below base 30, create a fluid communication between vacuum supply lumen 27 with suction ports 29.

Tissue clip magazine 22 includes a plurality of stationary holders 31 at base 30 of the magazine for holding one of the female and male members 11, 12 forming the tissue clip. In the embodiment shown in FIG. 4, three stationary holders 31 are disposed at substantially equidistant angular intervals around tube 21. Slider tracks 33 extend radially along base 30 from tube 21 to an outer wall 32 of magazine 22. Each slider track 33 engages a sliding clip holder 34, shown in FIG. 5a, at its end opposite to the end engaging a stationary clip holder 31. As mentioned previously, base 30 further includes a plurality of suction ports 29, preferably disposed on both sides of each slider track 33 between tube 21 and outer wall 32. The scope of invention is not limited to any particular number or arrangement of slider tracks or suction ports. Any number or arrangement of slider tracks and ports can be provided depending on the desired results in securing the tissue fold.

A cross-sectional view taken from the side of clipping device 20 is shown in FIG. 5a. In this Figure, tissue clips 10 are shown loaded into tissue clip magazine 22. Only one set of tissue clips, clip holders (stationary and sliding), and slider track is shown in FIG. 5a, however the remaining sets that are not shown are configured and operate in the same manner. Similarly, due to the perspective of the cross-section shown in the Figure, only endoscope lumen 25 and cable lumen 26 are shown. Tissue clips 10 are loaded in magazine 22 with one of the female and male members 11 and 12, respectively, engaged with stationary clip holder 31 and the other engaged with sliding clip holder 34. The clips can be held in pockets created in the clip holders, with the pockets carrying a plurality of fingers that are configured to form an interference fit with the tissue clip plates. Preferably, female member 11 engages with stationary clip holder 31 and male member 12 engages with sliding clip holder 34, as shown in the embodiment of FIG. 5a. Tissue clip magazine 22 preferably has a depth large enough to hold a plurality of tissue clip members stacked on top of each other. In a preferred form of the invention, each pair of clip holders (i.e. stationary clip holder 31 and sliding clip holder 34) holds two tissue clips 10, i.e. two female members 11 disposed one over the other and two male members 12 disposed one over the other. In the specific embodiment shown, the tissue clip magazine may install six tissue clips in a single insertion and actuation of clipping device 20. More or less tissue clips may be installed in a single actuation depending on the specific construction of the magazine and clip holders.

With reference to FIG. 5b, the engagement of sliding clip holder 34 and slider track 33 will now be explained. FIG. 5b is a cross-sectional perspective of tissue clip magazine 22 and sliding clip holder 34 taken from line B-B' in FIG. 5a. As shown in FIG. 5b, sliding clip holder 34 includes a narrow portion 38 at its base that is configured to fit snugly within slider track 33. Preferably, the slider track and the narrow portion either are made of, or are lined with, materials that reduce friction between the contacting surfaces to permit smooth movement of sliding clip holder 34 along slider track 33. Slider track 33 opens below base 30 into a channel 36 having a width wider than slider track 33. A channel-engaging member 39 depends from narrow portion 38 of sliding clip holder 34 and is moveably disposed within channel 36. As with slider track 33 and narrow portion 38, preferably, the materials selected for channel 36 and channel-engaging member 39 should minimize frictional effects.

Referring again to FIG. 5a, cable 28 extends from a proximal end of clipping device 20 through cable lumen 26 to a pulley 35 disposed between cable channel lumen 26 and channel 36. From pulley 35, cable 28 extends through channel 36 and a connects to channel-engaging member 39. Preferably, cable 28 branches into a plurality of cables, for example, one for each channel. Each of the branched plurality of cables in turn connects respectively to each of a plurality of pulleys provided in each channel. Thus, as an upward force is exerted on cable 28, shown by the vertical arrow in FIG. 6, pulley 35 rotates and the branch of cable 28 within channel 36 pulls channel-engaging member 39 through channel 36, imparting motion to sliding clip holder 34 along slider track 33. Channel-engaging member 39 attaches to a spring 37 on a side opposite to where cable 28 attaches, shown in FIG. 7. Thus, release of the upward force on cable 28 causes sliding clip holder 34 to spring back into its original position near outer wall 32 of tissue clip magazine 22. Female members 11 and male members 12, once secured through the tissue fold to one another, are held together with a force sufficient to cause them to be released from the interference fit with the fingers of clip holders 31 and 34 as the clip holders are pulled away from members 11 and 12.

Figure 8:
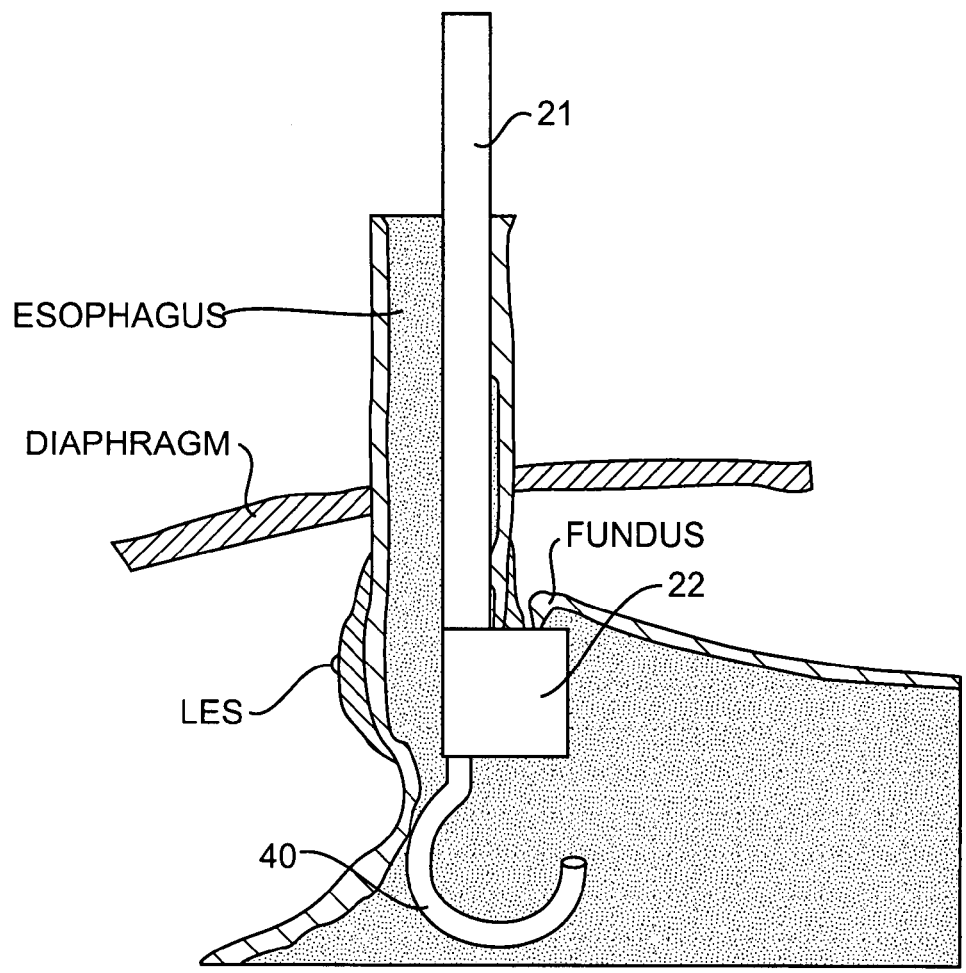
FIG. 8 is a side view of an embodiment of the clipping device of the present invention shown inserted into the stomach through the esophagus with an endoscope fed through the endoscope lumen to provide vision and the tissue clip magazine shown in position to form the tissue fold of the fundus onto the esophagus.

Using the embodiments of clipping device 20 and tissue clips 10 according to the present invention described above, the fundoplication procedure is performed in the following manner. Clipping device 20 is loaded with six tissue clips at the three substantially evenly-spaced angular locations around the semi-circle formed by tissue clip magazine 22, as described above with reference to FIG. 4. The loaded clipping device 20 is then inserted through the esophagus into the stomach. Referring to FIG. 8, an endoscope 40, fed through endoscope lumen 25, provides vision to the stomach so that tissue clip magazine 22 can be positioned in the region of the fundus to be folded and secured to the esophagus.

During the positioning of tissue clip magazine 22, a vacuum source, connected to vacuum lumen 27, creates a suction at suction ports 29 due to the fluid communication provided by the ducts as discussed above. With the vision provided by endoscope 40, clipping device 22 is pulled upward toward the region of the fundus wall to be secured. As clipping device 22 is pulled upward, the suction provided by suction ports 29 draws the fundus wall and the esophagus wall toward base 30 of tissue clip magazine 22. Once these walls have been drawn into tissue clip magazine 22 to create a tissue fold, an actuating mechanism connected to cable 28 at the proximal end of cable lumen 25 operates to pull cable 28 upward. As a result of this force, cable 28, connected to channel-engaging member 39, pulls member 39 through channel 36, moving sliding clip holder 34 along slider track 33 toward stationary clip holder 31. As sliding clip holder 34 moves toward stationary clip holder 31, engaging members 14 eventually pass through apertures 13 to form engaged tissue clips 10 to secure the tissue fold. The force exerted on cable 28 is large enough to enable engaging members 14 to pierce the thickness of the tissue fold and be driven through apertures 13 in female member 11. The actuating mechanism provided to create the upward force on cable 28 can be a handle that is turned manually, an automatic winding reel, or other suitable like actuators known to those skilled in the art.

Figure 9:
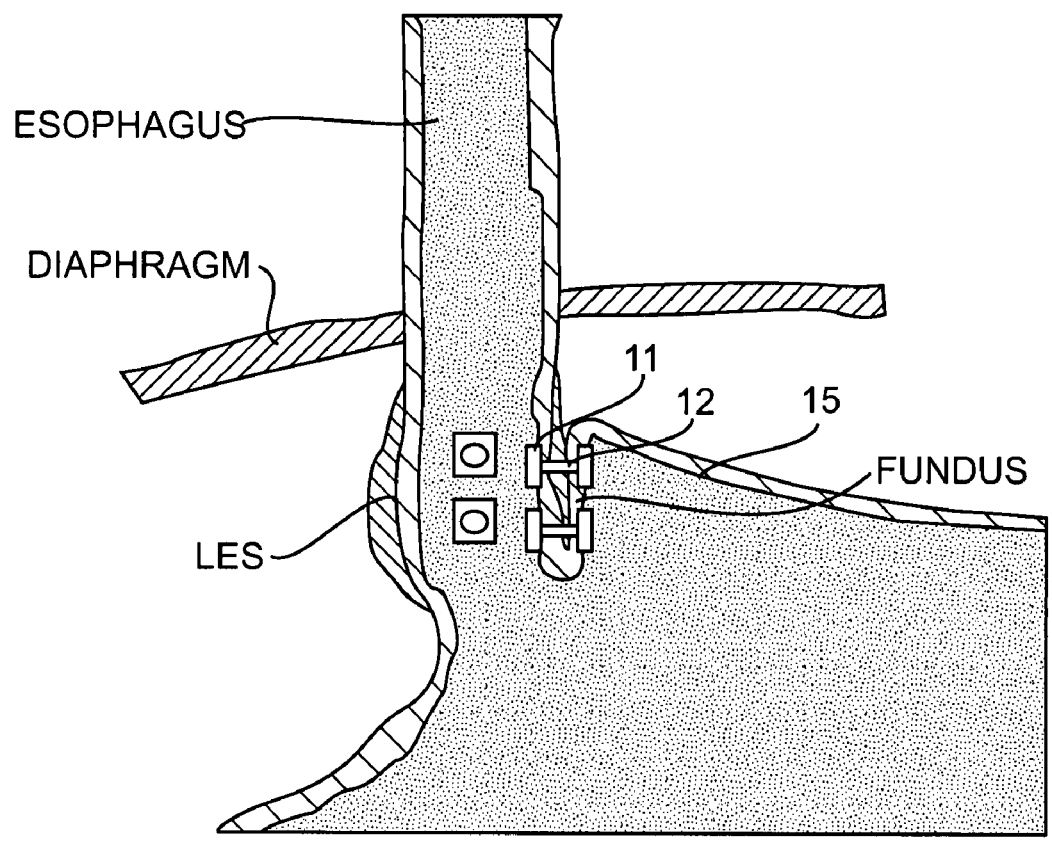
FIG. 9 is a cross-sectional view of a portion of the esophagus and stomach shown with tissue clips installed in a semicircular array to secure the fold of tissue created between the fundus and the esophagus.

After clipping device 20 has been actuated and tissue clips 10 have been formed, a tissue fold secured at angular positions around the esophagus results, as shown in FIG. 9. The uniform depth of tissue clip magazine 22, and the uniform spacing (both radially and vertically) of tissue clips 10, results in a tissue fold that is secured uniformly and quickly in a single insertion of the endoluminal device.

After tissue clips 10 have been installed, the force on cable 28 is removed and sliding clip holders 34 spring back into their original position, releasing male members 12. Clipping device 20 can then be removed from the stomach. Tissue clips 10 remain to secure the fundus wall to the esophagus wall preferably until natural adhesion of the two tissues occurs. A sclerosing agent can be injected-onto the tissue fold to facilitate the natural adhesion process. Eventually and preferably, tissue clips 10 disintegrate and fall away from the naturally-adhered fold.

It will be apparent to those skilled in the art from consideration of the specification and practice of the invention disclosed herein that various modifications and variations can be made in both the tissue clip and the clipping device of the present invention. For example, the tissue clip, and the tissue clip magazine for holding the tissue clip, may be provided in different sizes, such as, for example, small, medium, and large, for use with children, average-sized, and larger patients, respectively. However, it is important that the entire device be configured to fit in the esophagus, or other part of the body, depending on the particular endoluminal procedure being performed. Additionally, the number of tissue clips used to secure the tissue fold may be altered and the tissue clip magazine may be altered accordingly to house a different number of clips in both the radial and vertical directions. In addition, additional lumens may be provided in the tube so that additional devices may be inserted onto the esophagus and stomach to perform additional operations.

The particular use of both the tissue clip and the clipping device in conjunction with a Nipple Fundoplication procedure is illustrative only. It is considered to be within the scope of this invention to use these devices with other endoluminal procedures, as well as for purposes outside of the medical industry that may require insertion and installation of fasteners through small spaces.

Therefore, the invention in its broader aspects is not limited to the specific details and illustrative examples shown and described in the specification. It is intended that departures may be made from such details without departing from the true spirit or scope of the general inventive concept as defined by the following claims and their equivalents.

What is claimed is:
1. A device for securing a tissue fold, comprising:
an elongate tube having a longitudinal axis and a proximal end;
a distal member disposed on a distal end portion of the tube, the distal member comprising a base extending laterally from the tube and an outer wall extending substantially upright from the base toward the proximal end of the elongate tube, the elongate tube, the base, and the outer wall defining an opening configured to receive the tissue fold;
a plurality of tissue clips disposed in the distal member for securing the tissue fold received in the opening; and a drawing mechanism configured to draw the tissue fold into the opening, wherein the drawing mechanism comprises a suction port proximate the opening.

2. The device of claim 1, wherein the tube and the distal member are configured to be inserted endoluminally through an esophagus into a stomach to secure a fundus wall to an esophagus wall.

3. The device of claim 1, wherein the plurality of tissue clips are disposed radially around the longitudinal axis of the tube.

4. The device of claim 1, wherein each of the tissue clips comprises a male member and a female member configured to engage one another.

5. The device of claim 4, wherein the distal member comprises a first clip holder for holding at least one of the male members and a second clip holder for holding at least one of the female members, the first and second clip holders disposed substantially opposite to each other, at least one of the first and second clip holders is movable relative to the other.

6. The device of claim 5, further comprising an actuator proximate the proximal end of the tube, wherein actuation of the actuator imparts motion on at least one of the first and second clip holders so as to cause engagement between the at least one of the male members and the at least one of the female members.

7. The device of claim 5, wherein the distal member comprises multiple pairs of first and second clip holders arranged radially around the longitudinal axis of the tube.

8. The device of claim 7, further comprising an actuator proximate the proximal end of the tube, wherein actuation of the actuator simultaneously imparts motion on at least two of the multiple pairs of the first and second clip holders, thereby causing simultaneous engagements of multiple pairs of the male and female members.

9. The device of claim 1, further comprising an actuator proximate the proximal end of the tube, wherein actuation of the actuator simultaneously installs at least two of the plurality of tissue clips to secure the tissue fold.

10. The device of claim 1, wherein the tube comprises a lumen configured to receive an endoscope.

11. The device of claim 1, wherein the outer wall forms a semi-circular wall around the longitudinal axis of the tube.

12. A method for securing a tissue fold, comprising:
providing a distal member having a plurality of tissue clips disposed on a distal end portion of a tube, the distal member having a base extending laterally from the tube and an outer wall extending substantially upright from the base toward the proximal end of the elongate tube, the elongate tube, the base, and the outer wall defining an opening configured to receive the tissue fold;
positioning the distal member adjacent the tissue fold;
drawing at least a portion of the tissue fold into the opening by suctioning the portion into the opening; and
deploying at least one of the plurality of tissue clips to the tissue fold, thereby securing the tissue fold.

13. The method of claim 12, further comprising inserting the distal member endoluminally through an esophagus into a stomach, and the tissue fold includes a fundus wall and an esophagus wall.

14. The method of claim 12, wherein deploying at least one of the plurality of tissue clips comprises simultaneously installing the plurality of tissue clips to the tissue fold.

15. The method of claim 12, wherein the plurality of tissue clips are disposed radially around the longitudinal axis of the tube.

16. The method of claim 12, wherein:
each of the tissue clips comprises a male member and a female member configured to engage one another,
the distal member comprises a first clip holder for holding at least one of the male members and a second clip holder for holding at least one of the female members, and
the first and second clip holders are disposed substantially opposite to one another.

17. The method of claim 16, wherein deploying at least one of the plurality of tissue clips comprises moving at least one of the first and second clip holders toward the other, so as to cause engagement between the at least one of the male members and the at least one of the female members.

18. The method of claim 16, wherein the distal member comprises multiple pairs of the first and second clip holders arranged radially around the longitudinal axis of the tube, and deploying at least one of the plurality of tissue clips comprises actuating an actuator position at a proximal end portion of the tube to simultaneously impart motion on at least two of the multiple pairs of the first and second clip holders, thereby causing simultaneous engagements of multiple pairs of the male and female members.

19. A device for securing a tissue fold, comprising:
an elongate tube having a longitudinal axis and a proximal end;
a distal member disposed on a distal end portion of the tube, the distal member comprising a base extending laterally from the tube and an outer wall extending substantially upright from the base toward the proximal end of the elongate tube, the elongate tube, the base, and the outer wall defining an opening configured to receive the tissue fold; and
a plurality of tissue clips disposed in the distal member for securing the tissue fold received in the opening, wherein each of the tissue clips includes a male member and a female member configured to engage one another.

20. A method for securing a tissue fold, comprising:
providing a distal member having a plurality of tissue clips disposed on a distal end portion of a tube, the distal member having a base extending laterally from the tube and an outer wall extending substantially upright from the base toward the proximal end of the elongate tube, the elongate tube, the base, and the outer wall defining an opening configured to receive the tissue fold, wherein each of the tissue clips comprises a male member and a female member configured to engage one another, wherein the distal member includes a first clip holder for holding at least one of the male members and a second clip holder for holding at least one of the female members, and wherein the first and second clip holders are disposed substantially opposite to one another;
positioning the distal member adjacent the tissue fold;
drawing at least a portion of the tissue fold into the opening; and
deploying at least one of the plurality of tissue clips to the tissue fold, thereby securing the tissue fold.

* * * * *